United States Patent
Agrawal et al.

(10) Patent No.: US 8,217,211 B2
(45) Date of Patent: *Jul. 10, 2012

(54) PROCESS FOR PRODUCING LIQUID HYDROCARBON BY PYROLYSIS OF BIOMASS IN PRESENCE OF HYDROGEN FROM A CARBON-FREE ENERGY SOURCE

(75) Inventors: Rakesh Agrawal, West Lafayette, IN (US); Manju Agrawal, West Lafayette, IN (US); Navneet R. Singh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 690 days.

This patent is subject to a terminal disclaimer.

(21) Appl. No.: 12/199,425

(22) Filed: Aug. 27, 2008

(65) Prior Publication Data
US 2009/0082604 A1     Mar. 26, 2009

Related U.S. Application Data
(60) Provisional application No. 60/968,194, filed on Aug. 27, 2007.

(51) Int. Cl.
*C07C 1/00*     (2006.01)
*C10L 3/00*     (2006.01)
*C12M 1/00*     (2006.01)
(52) U.S. Cl. ...... 585/240; 585/242; 48/127.7; 48/197 R; 435/281; 435/308.1; 201/21
(58) Field of Classification Search .................. 585/240, 585/242; 48/127.1, 197 R; 423/418.2, 650; 201/21, 36; 202/96, 106; 422/190; 435/308.1, 435/281

See application file for complete search history.

(56) References Cited

U.S. PATENT DOCUMENTS
| | | | | |
|---|---|---|---|---|
| 4,678,860 A * | 7/1987 | Kuester | | 585/14 |
| 5,959,167 A * | 9/1999 | Shabtai et al. | | 585/242 |
| 6,846,402 B2 * | 1/2005 | Hemighaus et al. | | 208/14 |
| 6,863,878 B2 * | 3/2005 | Klepper | | 423/650 |
| 7,500,997 B2 * | 3/2009 | Norbeck et al. | | 48/127.7 |
| 7,578,927 B2 * | 8/2009 | Marker et al. | | 208/67 |
| 7,691,159 B2 * | 4/2010 | Li | | 44/605 |
| 7,816,570 B2 * | 10/2010 | Roberts et al. | | 585/240 |
| 7,833,512 B2 * | 11/2010 | Pulkrabek et al. | | 423/650 |

(Continued)

FOREIGN PATENT DOCUMENTS
WO    WO 2006/119118 A2    11/2006

OTHER PUBLICATIONS
Dinesh Mohan, Charles U. Pittman, Jr., and Philip H. Steele, "Pyrolysis of Wood/Biomass for Bio-oil: A Critical Review", Energy & Fuels (2006), 20, pp. 848-889.

(Continued)

*Primary Examiner* — Nina Bhat
(74) *Attorney, Agent, or Firm* — Cedric A. D'Hue; Bingham Greenebaum Doll LLP (57) ABSTRACT

In at least one embodiment of the present invention, a method for producing liquid hydrocarbons from biomass is provided. The method comprises pyrolizing the biomass with hydrogen ($H_2$) to form bio-oil. The bio-oil comprises alkanes, alkenes, alcohols, aldehydes, ketones, aromatics, hydrocarbons or mixtures thereof. The $H_2$ is formed from a carbon-free energy source.

25 Claims, 5 Drawing Sheets

Synergistic Integration of fermentation, $H_2$Bioil and $H_2$CAR Process

U.S. PATENT DOCUMENTS

2005/0232833 A1    10/2005    Hardy et al.
2007/0129449 A1    6/2007    Topf et al.

OTHER PUBLICATIONS

A.V. Bridgwater, G.V.C. Peacocke, "Fast pyrolysis processes for biomass", Renewable and Sustainable Energy Reviews (Apr. 2000); 1999 Elsevier Science Ltd., pp. 1-73.

Douglas C. Elliott, "Historical Developments in Hydroprocessing Bio-oils", Energy & Fuels (Jan. 2007), 21, pp. 1792-1815.

D.C. Elliott and G.G. Neuenschwander, "Liquid Fuels by Low-Severity Hydrotreating of Biocrude, Developments in Thermochemical Biomass Conversion", vol. 1, , Blackie Academic & Professional, London: (1996), pp. 611-621.

Mark C. Woods et al., Research and Development Solutions, LLC (RDS), "Cost and Performance Baseline for Fossil Energy Plants", vol. 1: Bituminous Coal and Natural Gas to Electricity—Final Report, (May 2007), pp. 1-508.

Mark J. Prins, Krzysztof J. Ptasinski, Frans J.J.G. Janssen, "Exergetic optimization of a production process of Fischer—Tropsch fuels from biomass", Fuel Processing Technology 86 (2004), pp. 375-389.

X. Li, J.R. Grace, A.P. Watkinson, C.J. Lim, A. Ergudenler, "Equilibrium modeling of gasification: a free energy minimization approach and its application to a circulating fluidized bed coal gasifier", Fuel 80 (2001), Department of Chemical and biological Engineering, University of British Columbia, pp. 195-207.

Zhao Yuehong, Wen Hao, Xu Zhihong, "Conceptual design and simulation study of a co-gasification technology", Energy Conversion and Management 47 (2006) pp. 1416-1428.

M. Ringer, V. Putsche, and J. Scahill, "Large-Scale Pyrolysis Oil Production: A Technology Assessment and Economic Analysis", NREL—National Renewable Energy Laboratory, Technical Report, NREL/TP-510-37779, (Nov. 2006), pp. 1-93.

M.D. Rutkowski, U.S. Department of Energy—"Hydrogen Program, Production Case Studies", http://www.hydrogen.energy.gov.h2a product studies.html, (2005), pp. 1-58.

M. K. Mann, U.S. Department of Energy—DOE H2A Analysis, http://www.hydrogen.energy.gov.h2a analysis.html, (2005). pp. 1-97.

U.S. Appl. No. 12/199,359, filed Aug. 27, 2008.

H. Bos, F. van Dongen, "Shell Coal Gasification Process", Gasification Conference Pittsburgh, Sep. 2005.

K. Aasberg-Petersen, T.S. Christensen, I. Dybkjaer, J. Sehested, M. Ostberg, R.M. Coertzen, M.J. Keyser, A.P. Steynberg, "Synthesis Gas Production for FT Synthesis" Studies in Surface Science and Catalysis, 2004.

Niels Fabricius, "Pearl GTL: Managing the Challenges of Scaling Up", Fundamentals of Gas to Liquids, 2005.

J.D. Rocha, C.A. Luengo, C.E. Snape, "Hydrodeoxygenation of Oils from Cellulose in Single and Two-Stage Hydropyrolysis," Renewable Energy, Pergamon Press, Oxford, GB, vol. 9, No. 1 (Sep. 12, 1996), pp. 950-953.

International Search Report—PCT/US2008/074463 (Feb. 18, 2009).

"The Hydrogen Economy, Opportunities, Costs, Barriers, and R & D Needs", National Research Council and National Academy of Engineering, (The National Academies Press, Washington, D.C.), (2004), pp. 1-257.

J.M. Tarascon & M. Armand., "Issues and challenges facing rechargeable lithium batteries", (Nature, vol. 414, Nov. 15, 2001), pp. 359-367.

Jason Hill, Erik Nelson, David Tilman, Stephen Polasky, and Douglas Tiffany, "From the Cover: Environmental, economic, and energetic costs and benefits of biodiesel and ethanol biofuels", (Proceedings of the National Academy of Sciences of the United States of America, (Nov. 2006), pp. 11206-11210.

Rakesh Agrawal, Navneet R. Singh, Fabio H. Ribeiro, and W. Nicholas Delgess, "Sustainable fuel for the transportation sector", Proceedings of the National Academy of Sciences of the United States of America, (Apr. 2007), pp. 4828-4833.

Rakesh Agrawal, Navneet R. Singh, "Process for Producing Synthetic Liquid Hydrocarbon", U.S. Appl. No. 60/843,678, filed Sep. 11, 2006.

A. V. Bridgwater, "Renewable Fuels and Chemicals by Thermal Processing of Biomass", Chemical Engineering Journal 91 (2003), pp. 87-102.

George W. Huber, Sara Iborra, and Avelino Corma, "Synthesis of Transportation Fuels from Biomass: Chemistry, Catalysts, and Engineering", Chem. Rev. (Jun. 2006), 106, pp. 4044-4098.

Hasan Ferdi Gercel, Ayse Eren Putun, Ersan Putun, "Hydropyrolysis of Extracted *Euphorbia rigida* in a Well-Swept Fixed-Bed Tubular Reactor", (Apr. 2001), Energy Sources, 24, pp. 423-430.

Ayse E. Putun, H. Ferdi Gercel, O. Mete Kockar, Ozgul Eg, Colin E. Snape and Ersan Putun, "Oil production from an arid-land plant: fixed-bed pyrolysis and hydropyrolysis of *Euphorbia rigida*", (Jan. 1996), Fuel, vol. 75, No. 11; pp. 1307-1312.

A.E. Putun, O.M. Kockar, S. Yorgun, H.F. Gercel, J. Andersen, C.E. Snape, E. Putun, "Fixed-bed pyrolysis and hydropyrolysis of sunflower bagasse: Product yields and compositions", Fuel Processing Technology, (Mar. 1995), pp. 46-62.

J. Dilcio Rocha, Carlos A. Luengo, Colin E. Snape, "The scope for generating bio-oils with relatively low oxygen contents via hydropyrolysis", Organic Geochemistry 30 (1999), pp. 1527-1534.

Kurt A. Rosentrater, "Expanding the Role of Systems Modeling: Considering Byproduct Generation from Biofuel Production", Ecology and Society, (2005), pp. 1-12.

R.L. Graham, R. Nelson, J. Sheehan, R.D. Perlack, and L.L. Wright, "Current and Potential U.S. Corn Stover Supplies", (2007), Agron. J. 99, pp. 1-11.

\* cited by examiner

Prior Art
Conventional Biomass Pyrolysis Process
Figure 1

Liquid Hydrocarbon Synthesis by Biomass Pyrolysis using carbon-free energy source
Figure 2

Figure 3
Synergistic Integration of fermentation, H₂Bioil and H₂CAR Process

'Sun to Fuel' power recoveries from the thermo-chemical (gasification/FT), Biological (fermentation), conventional pyrolysis and hydropyrolysis processes

Figure 4

'Sun to Fuel' power recovery for H₂Bioil process
Figure 5

PROCESS FOR PRODUCING LIQUID HYDROCARBON BY PYROLYSIS OF BIOMASS IN PRESENCE OF HYDROGEN FROM A CARBON-FREE ENERGY SOURCE

CROSS-REFERENCE TO RELATED APPLICATIONS

This application claims priority to U.S. Provisional Application No. 60/968,194, filed on Aug. 27, 2007, the entire contents of which are incorporated herein by reference.

TECHNICAL FIELD

The present invention relates generally to the synthesis of liquid hydrocarbon, and in particular to the synthesis of liquid hydrocarbon by pyrolysis of biomass in presence of hydrogen ($H_2$) from a carbon-free energy source.

BACKGROUND OF THE INVENTION

An important challenge facing society today is securing a sustainable fuel supply for the transportation sector. The transportation sector currently relies almost exclusively on liquid hydrocarbons as its energy source. The high energy density of gasoline, 8.88 kWh/liter, far exceeds that of proposed replacements $H_2$, 1.32 kWh/liter at 680 atm [1], or batteries, 175 Wh/kg [2]. Furthermore, the liquid hydrocarbon fuel distribution infrastructure is efficient and already in place.

Production of liquid fuels from biomass can help solve the problem of $CO_2$ emission from the transportation sector because $CO_2$ released from vehicle exhaust is captured during biomass growth. Currently, there are two major routes for conversion of biomass to liquid fuels: biological and thermochemical. In the biological process, fermentation of easily fermentable plant products, such as for example sugar, sucrose, dextrose and etc., to alcohols is achieved. These easily fermentable plant products can be extracted from corn kernels, sugar cane and etc. Major disadvantage of this pathway is that only a fraction of the total carbon in biomass is converted to the final desired liquid hydrocarbon fuel. Hill et al. calculate that conversion of all corn produced in USA to ethanol can meet 12% of entire US demand for gasoline which reduces to 2.4% after accounting for fossil fuel input [3].

Thermo-chemical routes include gasification of biomass to obtain synthesis gas (syngas), a mixture of carbon monoxide (CO) and hydrogen ($H_2$), and conversion of the syngas gas to liquid fuels using the Fischer-Tropsch (FT) process. A quick estimate can be made for the land area requirement to support the current oil consumption of 13.8 million barrels per day by the US transportation sector. For this purpose, biomass gasification data available from the Department of Energy (DOE) H2A analysis can be used. Assuming conversion of syngas to diesel to be 100% efficient by the FT process, then the land area required for a biomass growth rate of 15 ton/ha/yr and a gasifier efficiency of 74% is estimated to be about 2.67 million square km which represents 29% of the total US land area, thus suggesting that large scale production of liquid fuels from such a biomass conversion process is impractical.

Accordingly, further improvements and enhancements in the production of liquid fuels from biomass are desirable.

BRIEF SUMMARY OF THE INVENTION

Recently the Applicants discovered a thermo-chemical process where hydrogen from a carbon-free energy source is used in conjunction with the gasification of the biomass or a suitable carbon containing moiety [4, 5]. This preferably suppresses the formation of $CO_2$ and adjusts the ratio of $H_2$ to CO desired for the subsequent conversion of the syngas to a liquid fuel. An example of a subsequent conversion process is the use of a FT reactor to produce diesel. The process was nicknamed $H_2$CAR by the Applicants. The $H_2$CAR process minimizes/eliminates the release of carbon to atmosphere as $CO_2$ during the biomass to liquid fuel conversion process and thereby maximizes the yield of liquid fuel.

Figure 1:
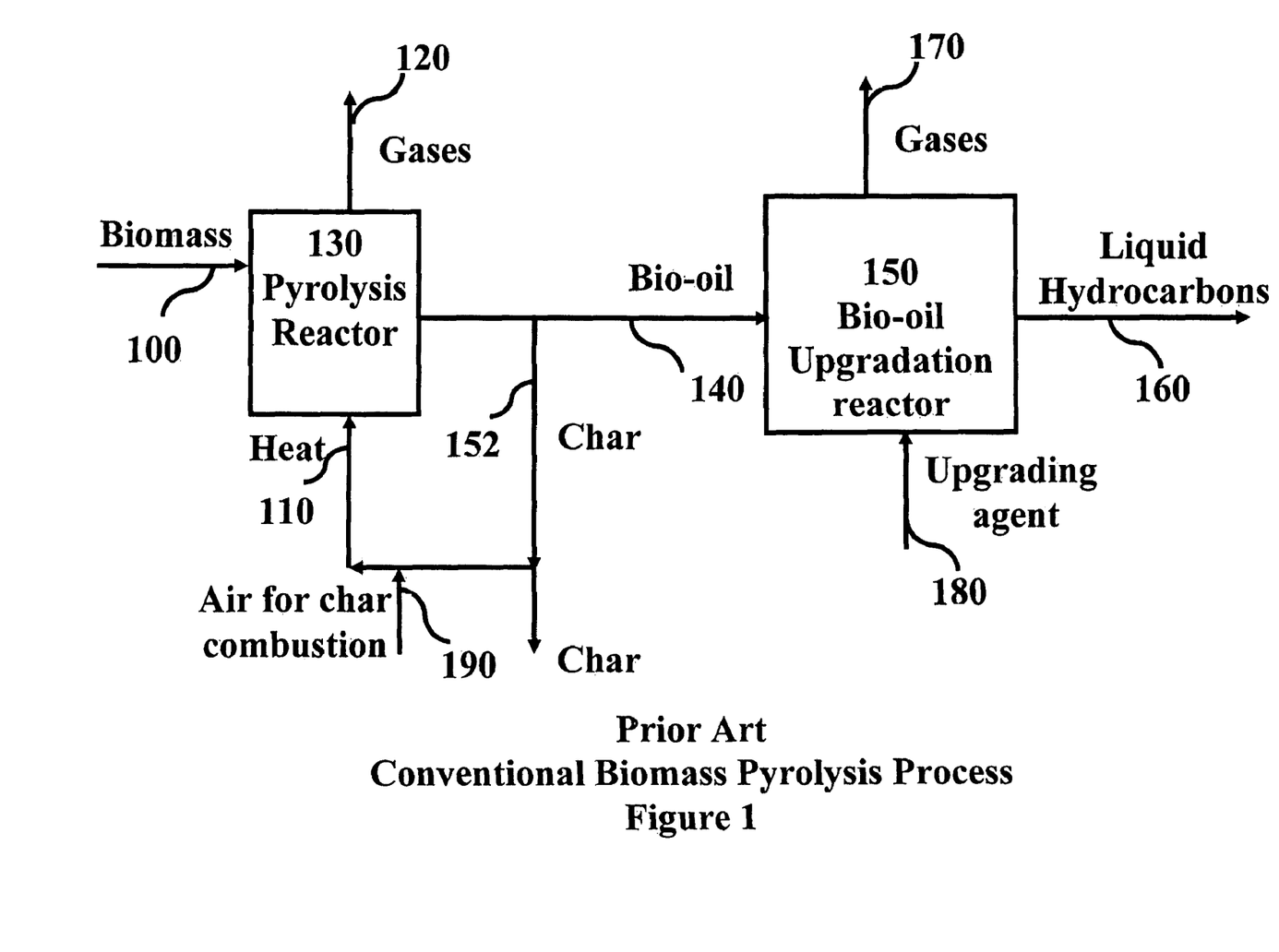
FIG. 1 depicts schematic representation of current biomass pyrolysis process.

Another alternative thermo-chemical route to convert biomass to liquid fuels is pyrolysis. A schematic of a typical biomass based pyrolysis process is shown in FIG. 1. The water content of biomass 100, such as for example switch grass, corn, wood and other cellulosic mass, is quite high. Therefore, the biomass 100 may be dried prior to feeding it to pyrolysis reactor 130. In one example, pyrolysis is a thermal decomposition of biomass 100 in absence of externally supplied oxygen [6]. Depending on temperature, heating rate and residence time, pyrolysis forms varying quantities of liquid, solid and gaseous products.

In at least one embodiment of the present invention, pyrolysis generally includes fast pyrolysis and in a preferred mode, pyrolysis is carried out as fast pyrolysis. Fast pyrolysis preferably yields large quantities of liquid fuel which is favored by moderate temperatures (e.g. about 400 to 600° C.) and short residence time (most preferably about 2 seconds or less) [6].

In a typical pyrolysis reactor, reaction heat can be supplied by hot walls, hot tubes, hot gas injection, hot gas recycle, or combinations thereof [7]. Char 152 may be separated from pyrolysis vapors 120 in cyclone separator and pyrolysis vapors may be rapidly quenched to obtain bio-oil 140. Non-condensable gases and char are usually combusted to supply process heat for the pyrolysis process and excess heat may be converted to electricity. Bio-oil formed directly from fast pyrolysis, however, may not be suitable for replacement of diesel or gasoline due to its low heating value, solid content, high viscosity, chemical instability etc [7]. Bio-oil produced as such has an energy content that is nearly half of petroleum and is similar to original biomass (~17 MJ/kg) due to extremely high oxygen contents (~35-40 wt %). Furthermore, such bio-oils do not easily blend with petroleum products. Accordingly, bio-oil upgrading may be performed by hydro-deoxygenation (HDO) or zeolite upgrading 150. HDO refers to removal of oxygen (O) in biomass in the form of water and the HDO is carried out with high-pressure hydrogen in presence of heterogeneous catalyst 180 at moderate temperatures of about 300 to 600° C. [7]. Zeolite upgrading also involves O removal and improving thermal stability by using temperatures between about 350 and 500° C., atmospheric pressure and gas-hourly space velocity of around 2 $hr^{-1}$. Zeolite upgrading is feasible at atmospheric pressure and no $H_2$ is required decreasing the operating cost, however, poor hydrocarbon yields 160 and high yields of coke limit the usefulness of this process [7]. Bio-oils tend to polymerize and condense with time during shipment and storage, and are known to cause coking and gum formation in the HDO reactor and associated lines 160 and 170.

Pütün et al. studied the effect of presence of hydrogen on extracted *Euphorbia rigida* [8, 9] and sunflower bagasse [10] pyrolysis. Pyrolysis of *Euphorbia rigida* yields 22 wt % bio-oil at 550° C. and 7 K/min in absence of hydrogen. The highest bio-oil yield of 41.5 wt % was obtained at 300 K/min at a temperature of 550° C. in presence of 150 bar $H_2$ pressure in a fixed bed reactor. Notably, not only does the yield of bio-oil nearly doubled in presence of hydrogen but the calorific value of the hydropyrolysis oil also increases as compared to the conventional pyrolysis oil (~42 MJ/kg vs. ~17 MJ/kg). In a similar study carried out for sunflower bagasse, Pütün et al. [10] reported a maximum bio-oil yield of 35-40% for a range of particle sizes (0.4-1.8 mm), sweep gas ($N_2$) flow rates varying from 0-600 $cm^3$/min and heating rates of 7 or 40 K/min. Bio-oil yields up to 50% were possible for hydropyrolysis for a temperature range and a pressure range of 500-600° C. and 50-150 bar, respectively. The bio-oil yield increased by ~10% using $H_2$ for same biomass species and bio-oil formed had higher calorific value. Hydropyrolysis is defined herein as pyrolysis in presence of at least some externally supplied $H_2$. The externally supplied $H_2$ excludes any $H_2$ co-generated during pyrolysis. In both these studies, the hydropyrolysis formed bio-oil had lesser oxygen content as compared to the pyrolysis formed bio-oil.

Conventional wisdom points that $H_2$ needed for hydropyrolysis will either be derived from steam reforming of methane or gasification of coal or biomass which will lead to the discharge of $CO_2$ in the atmosphere. Rocha et al. suggests using gasification to supply the needed $H_2$ for hydropyrolysis [11]. Currently, almost all the hydrogen used in the chemical conversion processes are derived from fossil fuels such as methane. During conversion of methane to $H_2$, large quantities of $CO_2$ are produced. This $CO_2$ is generally vented with the loss of hydrocarbons occurring.

Notably, the thermo-chemical processes based on biomass gasification and subsequent FT processing are quite capital intensive. For these processes to be economical, they tend to be set up as large plants requiring biomass to be shipped over large distances. This problem is further compounded by the fact that biomass has a much lower volumetric energy density than other fuel sources. Furthermore, FT reactors produce a large quantity of low level heat contributing to the overall inefficiency of the process. A conventional biomass gasifier with a FT reactor has an overall process efficiency of less than 40%. Large scale biomass gasifiers are also not amenable to intermittent operation. On the other hand, conventional pyrolysis units can be built on relatively smaller scale and have biomass conversion efficiencies in the range of about 65%-75%. The small scale plant preferably requires that less biomass will be shipped to any particular plant. This may have a significant impact by reducing the distances for shipping biomass. Also, pyrolysis units may require much less capital per plant and are amenable to intermittent operation. However, the conventional pyrolysis plants may suffer from a major drawback that the bio-oil products from these plants may have extremely high oxygen content (~35-40 wt %) and their energy content may be nearly half of petroleum and be similar to biomass (~17 MJ/kg). Furthermore, the conventional produced bio-oil products do not easily blend with petroleum products. Moreover, the bio-oils tend to polymerize and condense with time during shipment and storage. As a result, such bio-oils are generally unsuitable for use in internal combustion engine used by the transportation sector.

In at least one embodiment of the present invention, a biomass conversion process is provided that is efficient, can be built on a relatively small scale and provides stable bio-oil with high energy content that can be either directly used by the transportation sector or requires minimal additional processing. In one aspect, the present invention uses $H_2$ from a carbon-free energy source during pyrolysis of biomass to increase the 'Sun to Fuel' power recovery per unit land area. This increase in solar energy utilization will decrease the land area required to produce a given quantity of liquid. Processes reported in the literature on the synthesis of liquid hydrocarbon fuels from biomass are not able to meet the need for the entire US transportation sector because biomass can only store 5 $W/m^2$ of 1000 $W/m^2$ available from Sun at a typical biomass growth efficiency of about 0.52% after accounting for agricultural energy input. In one embodiment, the utilization of power available from the Sun per unit land area is significantly increased as compared to the prior art processes. Power available from Sun can be stored at ~70 $W/m^2$ in $H_2$ via solar thermal electric or Photovoltaic (PV). Combining biomass pyrolysis and carbon-free $H_2$ for liquid fuel production preferably increases the power utilization from the Sun significantly while producing bio-oil with a relatively higher energy density.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION OF THE INVENTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Embodiments of the present invention provide a process for the synthesis of liquid hydrocarbons where hydrogen from a carbon-free energy source is used in the conversion process of biomass to form liquid fuels through pyrolysis. In one embodiment, the biomass material contains carbon and comprises any plant, tree material or a mixture thereof that grows in the earth's ecosystem. Some examples include switch grass, poplar tree, sugar cane, corn, tree barks, aquatic material including algae, plankton, or any other suitable plant and/or animal from the oceans, estuaries, lakes, rivers, streams, wetlands, and ponds, and/or etc. The carbon-free energy sources include renewable sources and nuclear. Examples of renewable sources are solar, wind and hydropower. The energy from the carbon-free energy source can be easily converted to hydrogen. Sources such as wind and hydropower can be used to provide electricity. This electricity can then be converted to $H_2$ through electrolysis of water. In another embodiment, other sources such as solar and nuclear have additional options for providing $H_2$ through a suitable thermo-chemical cycle that directly uses high temperature heat. Some examples of thermo-chemical cycles are sulfur-iodine (SI) and calcium-bromine-iron cycles [12]. Also included are the advancements being made whereby solar energy is directly used to recover $H_2$ from water. The $H_2$ from the carbon-free energy source may be used to supply all the energy needs during pyrolysis in addition to being a reactant for the chemical reactions that occurs during pyrolysis. For example, some of the $H_2$ can be combusted to supply heat that may be needed for pyrolysis. Furthermore, heat and/or electricity can also be used from the carbon-free energy source to supply the thermal energy needed for pyrolysis. In at least one embodiment of the present invention, $H_2$, heat and/or electricity can be derived from a single or multiple carbon-free energy sources and at least a portion of the biomass is fast pyrolyzed with the $H_2$ to form a liquid stream called bio-oil.

A conventional fast pyrolysis reactor 130 is an apparatus where biomass 100 is fed and a mechanism to supply heat 110 and air 190 for the pyrolysis is provided in FIG. 1. The gases exiting the pyrolyzer are generally sent to a cyclone (not shown in FIG. 1) where solid char products 152 are separated. This char is burned to provide heat for pyrolysis and drying. Next, bio-oil and gaseous products are separated by cooling to low temperature. A part of the gases in line 170 can also be used to supply heat for pyrolysis or used as fluidizing gas [7] and flue gases from char and gas combustion can be used for biomass drying.

Figure 2:
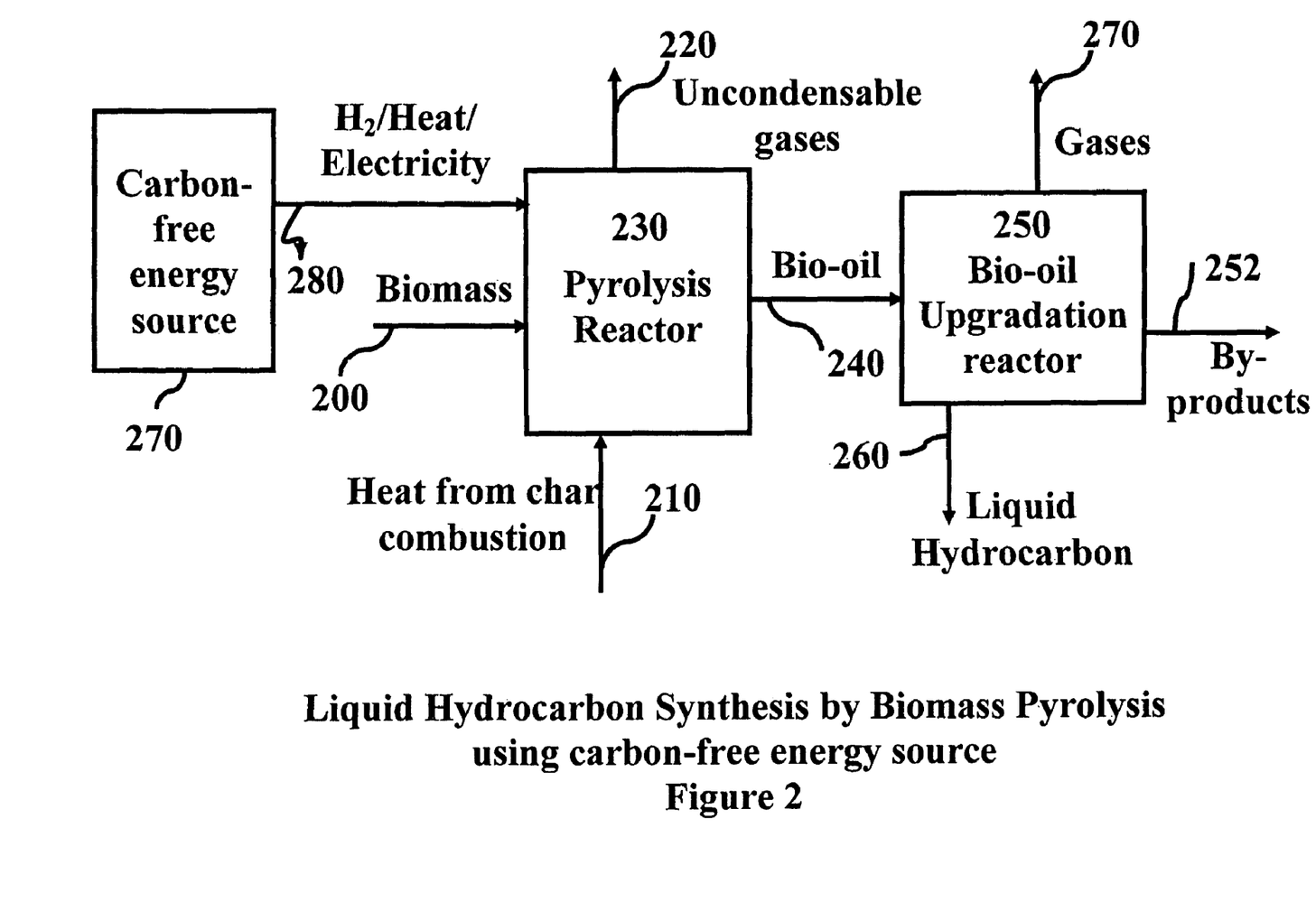
FIG. 2 depicts a generalized schematic representation of the liquid hydrocarbon synthesis from biomass pyrolysis using carbon-free energy source in accordance with one embodiment of the present invention.

An embodiment of the present invention is shown in FIG. 2. Biomass in stream 200 is fed for fast pyrolysis to unit 230. Preprocessing of biomass to prepare it as feed for pyrolysis, e.g. pre-drying, is not shown in FIG. 2 but may be included in an operating plant. Heat from char combustion in stream 210 is also supplied to the pyrolysis reactor. The exhaust 220 and 240 from the pyrolysis is further processed (cyclone separator for char removal and gas-liquid separation and condenser for bio-oil separation from gaseous molecules, not shown in FIG. 2) and constitutes the pyrolysis step. $H_2$ from a carbon-free source 270 is sent through line 280 to the biomass pyrolysis unit 230. In addition to the $H_2$ in line 280, additional energy from the carbon-free source can be potentially supplied as either heat and/or electricity. The supply of this energy decreases or preferably completely eliminates the need for any heat supply in line 210 which is from char combustion. Moreover, due to the use of $H_2$ from a carbon-free source, the bio-oil in line 240 will preferably contain more hydrogen atoms (H) and less oxygen atoms (O) as compared to conventionally produced biomass. Furthermore, under certain operating conditions, feeding of the $H_2$ from the carbon-free energy source will decrease the quantity of char fed to and separated by the cyclone separator. The bio-oil in line 240 is one example of bio-oil formed in accordance with the present invention, and the corresponding process and configuration is referred to as the "Hydrogen Bio-oil" ($H_2$Bioil) process.

In another embodiment $H_2$, heat or electricity from carbon-free energy is used to supply process heat for the fast pyrolysis process. Usually, all the char and gases formed during pyrolysis are combusted to supply process heat for the process. $H_2$Bioil can use carbon-free energy not only to provide process heat for hydropyrolysis but also for hydrogasification of char and gaseous molecules to convert it to light hydrocarbons such as methane (also called synthetic natural gas-SNG). To facilitate the conversion process of the gaseous molecules, such as for example CO and $CO_2$ to methane, a methanation catalyst, such as Nickel on a support, may be used.

In yet another embodiment of the present invention, $H_2$ from a carbon-free energy source is added in the gas-phase exhaust from the pyrolysis reactor before or after cyclone separator in presence of a catalyst(s), preferably HDO catalyst. This may improve the properties of the bio-oil, such as for example producing bio-oil with higher heating value, low viscosity, higher chemical stability, etc. In one embodiment, HDO is carried at temperature lower than 500° C., more preferably less than 400° C. and most preferably around or below about 350° C.

Fast hydropyrolysis may be done in the presence of a suitable HDO catalyst. For this purpose, if heat for hydropyrolysis is provided through a fluidized bed, then catalyst particles can either be mixed with the material of the fluidized bed or supported on the particles being fluidized. An example would be sand used as a circulating fluidized material to supply heat for fast hydropyrolysis. In such a case, the HDO catalyst may either be mixed with the sand or supported on the sand particles. When the exhaust of the hydropyrolysis reactor contains solids, it may be sent through a cyclone to separate solids. If the hydropyrolysis is effective by itself to provide a bio-oil with lower oxygen content and higher energy density, then, the separated exhaust may be rapidly quenched to condense bio-oil. In one embodiment, the energy density of the bio-oil is greater than 20 MJ/kg, preferably greater than 30 MJ/kg and most preferably greater than 35 MJ/kg. The higher density bio-oil may be usable in an internal combustion engine with relatively minimal processing.

If the separated hot gaseous stream from the exhaust of the hydropyrolysis reactor contains bio-oil whose energy density is to be further increased, then this gas stream may be sent to a HDO reactor containing suitable HDO catalyst. The temperature of the separated hot gaseous stream may be adjusted to a temperature that is suitable for the HDO reactor. Generally, as stated earlier, this may require some cooling prior to feeding the gas stream to the HDO reactor. The HDO reactor may be any suitable reactor configuration, such as for example a fixed bed, fluidized bed, etc. The HDO catalysts used in the HDO reactor can be chosen from an array of known HDO catalysts, such as for example, FeS, Ni—Co or Co—Mo on $\gamma$-$Al_2O_3$, or a newly developed catalyst. If needed, additional $H_2$ from the carbon-free energy source may be co-fed to the HDO reactor. The effluent from the HDO reactor may then be condensed to obtain a relatively low-oxygen, high energy density bio-oil product. Advantageously, the relatively low-oxygen, high energy density bio-oil may be directly used in many applications without further upgradation. In one embodiment, the pyrolysis reactor 230 comprises the hydropyrolysis reactor and the hydrodeoxygenation reactor as described.

In an embodiment of the present invention, a bio-oil upgradation reactor may be added to the $H_2$Bioil process in FIG. 2. In this scenario, the bio-oil stream 240 is sent to a bio-oil upgrading reactor system 250 containing either HDO or zeolite upgrading catalyst. Upgraded liquid hydrocarbons are obtained in stream 260, by-products in stream 252, and gases formed during bio-oil upgrading are shown in line 270. $H_2$ from the carbon-free energy source is also preferably used during the HDO process (bio-oil upgradation) for removal of oxygen (O) in the form of water and for the process heat needs of this process. Notably, in a conventional bio-oil upgradation reactor, nearly 20-30% of the carbon atoms in bio-oil are lost in the gas phase during bio-oil upgradation, decreasing the overall yield of the liquid fuel [7]. Use of $H_2$ from the carbon-free energy source in the upgrading reactor can reduce, minimize or completely eliminate this loss by converting CO and $CO_2$ to SNG, diesel or the alike through a FT process (FTD) using $H_2CAR$ process.

In another embodiment, the relatively low-oxygen, high energy density bio-oil may be shipped to a central refinery for further processing to form a specific liquid fuel molecule for the transportation sector as it is done with a petroleum crude feed to a refinery. The bio-oil could also be shipped to a chemical plant to make specific chemicals. In such scenarios, the advantage of at least one embodiment of the present invention is that by providing a higher energy density bio-oil, shipping more energy in a given volume is facilitated which may reduce the cost of shipping. Furthermore, this relatively low-oxygen and high energy density bio-oil may be more stable during shipping. Finally, shipping to a central refinery could be done from multiple hydropyrolysis ($H_2$Bioil) plants. This preferably provides a synergistic and economical solution as it may solve the shipment of low-density biomass over long distance by providing conversion of biomass to relatively high energy density bio-oil through the distributed $H_2$Bioil plants.

In one embodiment of the present invention, the bio-oil produced is a liquid hydrocarbon mixture containing one or more organic compounds from the group of alkanes, alkenes, alcohols, aldehydes, ketones, aromatics etc. A bio-oil liquid hydrocarbon fuel may contain one or more from the group of methanol, ethanol, long chain alcohols, alkanes, alkenes, aromatics, aldehydes, ketones, and substitutes aromatic compounds of these. When bio-oil is used as liquid hydrocarbon fuel, it is generally a material comprising carbon (C) and hydrogen (H) atoms that can exist in a closed system at normal temperature and pressure (20° C. and 1 atm) in a liquid state.

In at least one embodiment of the present invention, hydropyrolysis is performed as fast pyrolysis in the presence of hydrogen. As discussed previously, fast pyrolysis yields large quantities of liquid hydrocarbons which is favored by moderate temperatures (e.g., about 400 to 600° C.) and short residence time in the pyrolysis reactor (e.g., most preferably about 2 seconds or less). In the $H_2$Bioil process, the residence time within the hydropyrolysis reactor will be generally less than 1 minute, and preferably less than 10 seconds and most preferably around 2 seconds or less.

In yet another embodiment of the present invention, the fast pyrolysis reactor can operate without the injection or co-feeding of the $H_2$ from the carbon-free source. In this scenario, the fast pyrolysis reactor may operate at moderate temperatures (e.g. about 400 to 600° C.) and preferably with short residence times as suggested for the hydropyrolysis reactor. The solid char may be removed from the fast pyrolysis reactor exhaust stream, then $H_2$ from the carbon-free energy source may be mixed therewith and the resulting gaseous stream may be sent through the HDO reactor as described earlier. Preferably, the HDO reactor upgrades the bio-oil derived from the fast pyrolysis reactor using $H_2$ supplied from the carbon-free energy source. The catalyst and operating temperature range etc. may still be similar to those described earlier for the HDO reactor post the hydropyrolysis reactor. In this example, the fast pyrolysis of biomass in absence of $H_2$ from the carbon-free source and then subsequent use of the $H_2$ in the HDO reactor constitutes the use of $H_2O$ from the carbon-free energy source during the pyrolysis step in accordance with one embodiment of the present invention.

Similar benefits of using $H_2$ from solar-thermal electric or PV during fast hydropyrolysis is possible through the use of other carbon-free energy sources such as nuclear, etc. Also, hydropyrolysis performance may be enhanced at higher $H_2$ pressures, however, $H_2$ compression may be energy intensive. Accordingly, if an electrolyzer is used to make hydrogen from water, the electrolyzer may be operated at higher pressure by liquid water pressurization at relatively lower energy cost.

Figure 3:
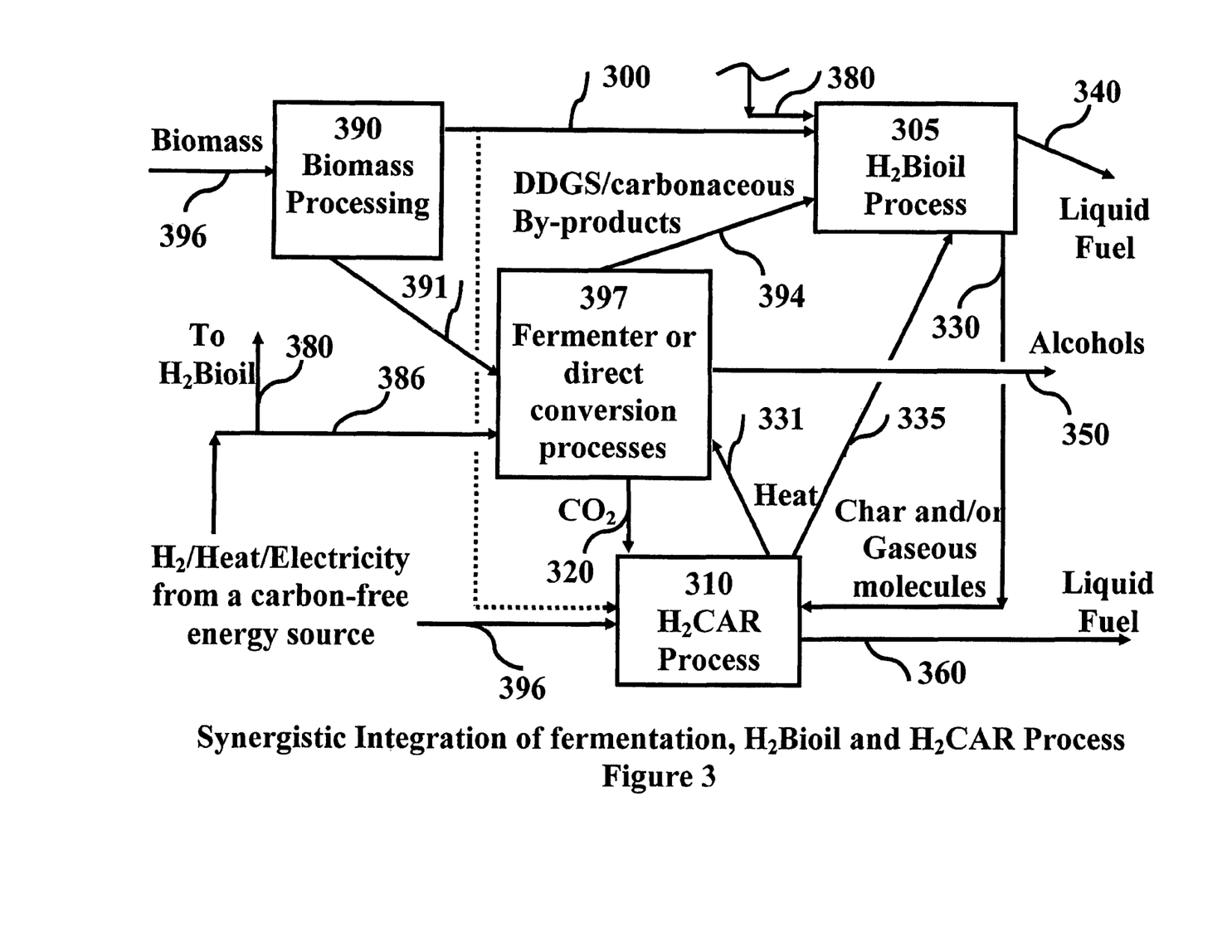
FIG. 3 depicts one of the possible schematic representations of the liquid hydrocarbon synthesis wherein sugary biomass are processed via fermenter using carbon-free energy, complex biomass as well as carbonaceous by-products from fermenter are fed to $H_2$Bioil process and $CO_2$, small gaseous molecules and any biomass is processes by $H_2$CAR process in accordance with one embodiment of the present invention.

In one embodiment, the biomass can have components that can easily be converted to liquid hydrocarbons by using micro-organisms. Examples include fermentation of different sugars, etc. to ethanol or butanol, etc. Such sugars can be obtained from corn kernels, sugar cane, etc. However, these crops may also contain cellulosic and other forms of biomass that are not easily processed by micro-organisms. Corn stover, sugarcane bagasse, etc. are some examples of such biomass. One embodiment of the present invention is synergistic integration of $H_2$Bioil process 305 with a fermentation unit 397 and a $H_2CAR$ process unit 310 as shown in FIG. 3. In the biomass processing unit 390, the biomass 396 may be split into two major streams. The biomass in 391 contains that portion of the original biomass in stream 396 which can be directly converted to liquid hydrocarbons by micro-organisms in unit 397. Another portion of the biomass from unit 390 that is difficult to handle in unit 397 is sent through line 300 to either the $H_2$Bioil process or the $H_2CAR$ process, but more preferably to the $H_2$Bioil process. If desired, Ethanol (stream 350) obtained from fermentation can be directly mixed with bio-oil. Most of the energy required for the ethanol process may be in the form of heat. This heat can be supplied from the carbon-free energy source, such as for example solar-thermal and/or nuclear (stream 386), or from high-level heat available from the gasifier (~1000° C.) and FT reactor (~300° C.) of the $H_2CAR$ process (stream 331). Ethanol fermentation may follow the one-third rule where ⅓ of corn grain is converted to ethanol, ⅓ to $CO_2$ and ⅓ to dried distillers grain solubles (DDGS) by mass [13]. DDGS and carbonaceous by-products can be sent via line 394 to the $H_2$Bioil process. If needed, heat from the $H_2CAR$ gasification reactor and/or FT reactor could also be used in the $H_2$Bioil process (stream 335). Any gaseous product from the $H_2$Bioil process with carbon containing molecules along with any available solid char byproduct (stream 330) may be sent to the $H_2CAR$ process for conversion to liquid fuel 360. Also, $CO_2$ (stream 320) from the fermenter unit 397 can be converted to liquid fuel by using $H_2CAR$ process unit 310 [4, 5]. The $H_2$ from the carbon-free energy source is provided through line 380 to the $H_2$Bioil process and through line 396 to the $H_2CAR$ process.

FIG. 3 shows the simultaneous integration of the $H_2$Bioil process with both the fermenter (397) and $H_2CAR$ (310) processes. Alternatively, the $H_2$Bioil process 305 may just be integrated with either the fermenter or the $H_2CAR$ processes. When the $H_2$Bioil process is integrated with one or the other of the two processes, then the unintegrated process and its associated streams may be eliminated from FIG. 3. This may lead to relatively simpler processes and may be adequate for many applications.

In one embodiment, biomass and $H_2$ are fed to a suitable high temperature location in the biomass pyrolysis process. It is to be understood that prudent practices to preheat such streams relative to other suitable process streams prior to feeding then at a high temperature may be followed. Use of heat exchanger network with proper pinch diagrams may be used. Such heat exchange practice may improve the overall efficiency of the process.

In at least one embodiment of the present invention, certain benefits may be realized. By using energy from a carbon-free energy source and combining it with biomass pyrolysis, power utilization for liquid fuel production from the Sun may increase significantly, leading to increased bio-oil yield. Specifically, when the carbon-free energy source is recovered as $H_2$, the novel manner disclosed herein in which $H_2$ is used in the $H_2$Bioil process with the biomass to increase yield of liquid hydrocarbon products is an important feature.

This process preferably solves the low volumetric energy density problem of biomass and $H_2$ simultaneously by combining them to produce a high density liquid fuel. Work has already begun on a number of methods for on-board $H_2$ storage for fuel cell applications and faces a number of challenges. Similarly, biomass harvesting and transportation is expected to be a major hurdle for the bio-energy scenario to evolve fully as volumetric energy density of biomass is only 7-10% of the volumetric energy density of coal.

In addition, gasifiers and FT processes are energy intensive and need to be large scale to be economical. Furthermore, these processes can not be scaled down easily or amenable to intermittent operation. On the other hand, biomass hydropyrolysis of the current operation can be operated economically at a much smaller scale and is amenable to frequent start-up and shut down so the operation of pyrolysis unit can be matched with the intermittent availability of $H_2$ from the carbon-free energy source. Small scale operation of hydropyrolysis will help to decrease the transportation distance often required for low volumetric energy density biomass and in some cases of $H_2$.

EXAMPLE 1

Figure 4:
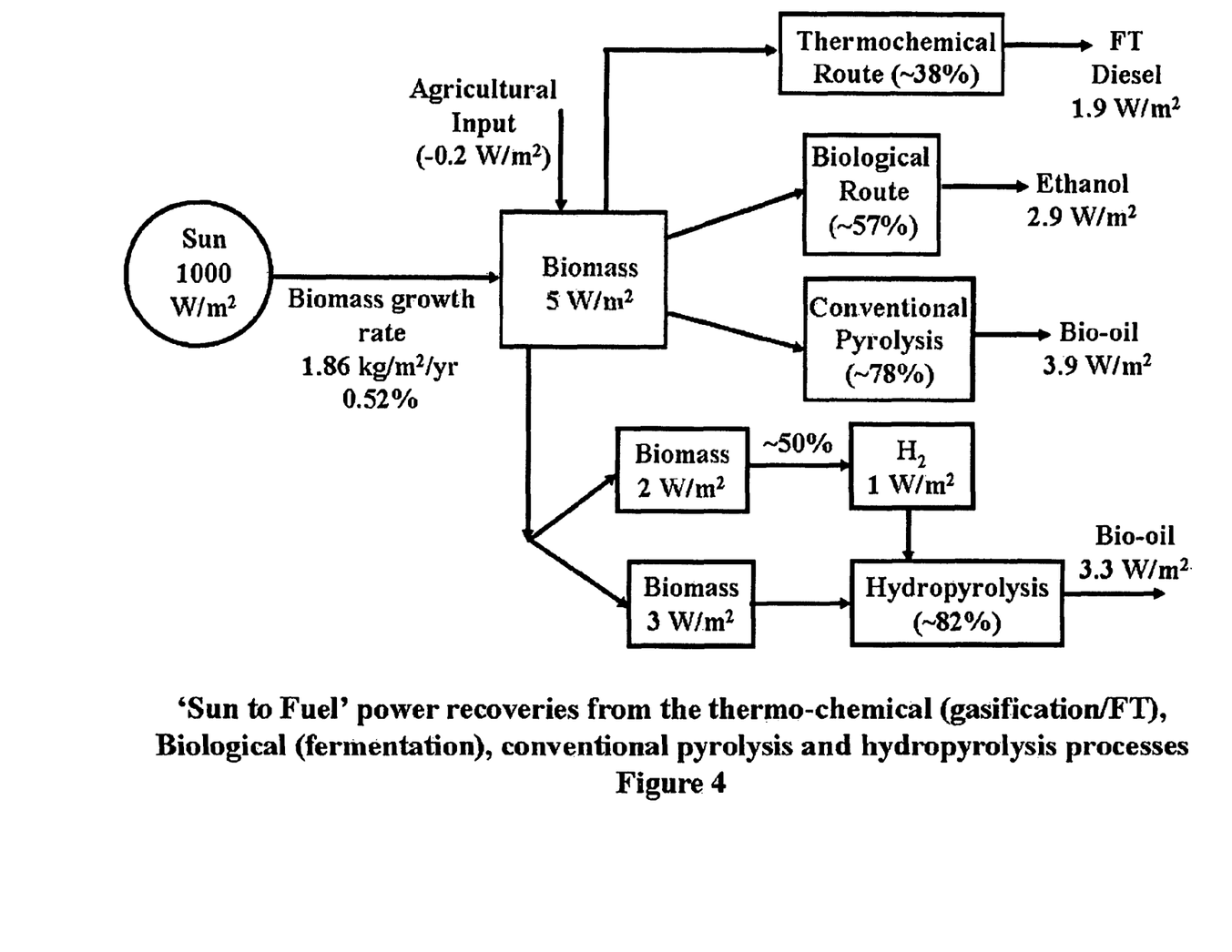
FIG. 4 depicts the 'Sun to Fuel' power recoveries from the Thermo-chemical (gasification/FT), Biological (fermentation), pyrolysis and hydropyrolysis processes.

To further illustrate the benefits of at least one embodiment of the present invention as compared to the prior art, the power utilization per $m^2$ of land area is depicted using various processes based on a solar insolation of 1000 $W/m^2$, which is a normalized value used for comparative purposes. The Annualized Energy Efficiency (AEE) based on the energy coming from Sun [4] and for a biomass growth rate of approximately 1.86 $kg/m^2/yr$ is calculated to be approximately 0.52% (Biomass assumed here is corn grown in US, annual productivity of which is approximately 9296 kg/ha [3]. Assuming a harvest index of approximately 0.5 [14], net biomass growth rate becomes approximately 1.86 $kg/m^2/yr$). Based on approximately 1000 $W/m^2$ available from the Sun, approximately 5.2 $W/m^2$ is stored in the form of biomass. Hill et al. reported 6.39 MJ/l ethanol as the agricultural energy input required to obtain this corn growth rate which translates to approximately 0.2 $W/m^2$ [3]. Accordingly, the net power stored in biomass is approximately 5 $W/m^2$. Depending on the energy efficiency of the process as shown in FIG. 4, approximately 1.9, 2.9 and 3.9 $W/m^2$ are stored in the final liquid fuel obtained from gasification followed by the FT process (thermo-chemical route), ethanol (biological route) and conventional pyrolysis processes respectively. In the hydropyrolysis process, $H_2$ can be used to remove oxygen content of bio-oil as $H_2O$ via HDO. There may be no need to remove all of the oxygen present in the bio-oil as a small quantity (<5 wt %) of oxygenate may facilitate combustion in internal combustion engines. A simple calculation shows that if all but approximately 4 wt % oxygen is removed as $H_2O$ improving the energy content of the bio-oil to approximately 42 MJ/kg, then, the energy efficiency of this process based on the energy content of biomass and $H_2$ available at the plant gate will be approximately 82%. In the hydropyrolysis process shown in FIG. 4, $H_2$ is derived from the gasification of nearly $\frac{2}{5}^{th}$ of the biomass. Energy efficiency of the conversion of biomass to $H_2$ is taken to be approximately 50% and the $H_2$ is used to hydropyrolyze the remaining $\frac{3}{5}^{th}$ of the biomass. The 'Sun to Fuel' power utilization for the hydropyrolysis process is approximately 3.3 $W/m^2$ which is less than 3.9 $W/m^2$ recovered via the conventional fast pyrolysis.

It should be noted that hydrogen derived from the gasification of any carbon containing moiety including biomass does not constitute hydrogen from a carbon-free energy source.

EXAMPLE 2

Figure 5:
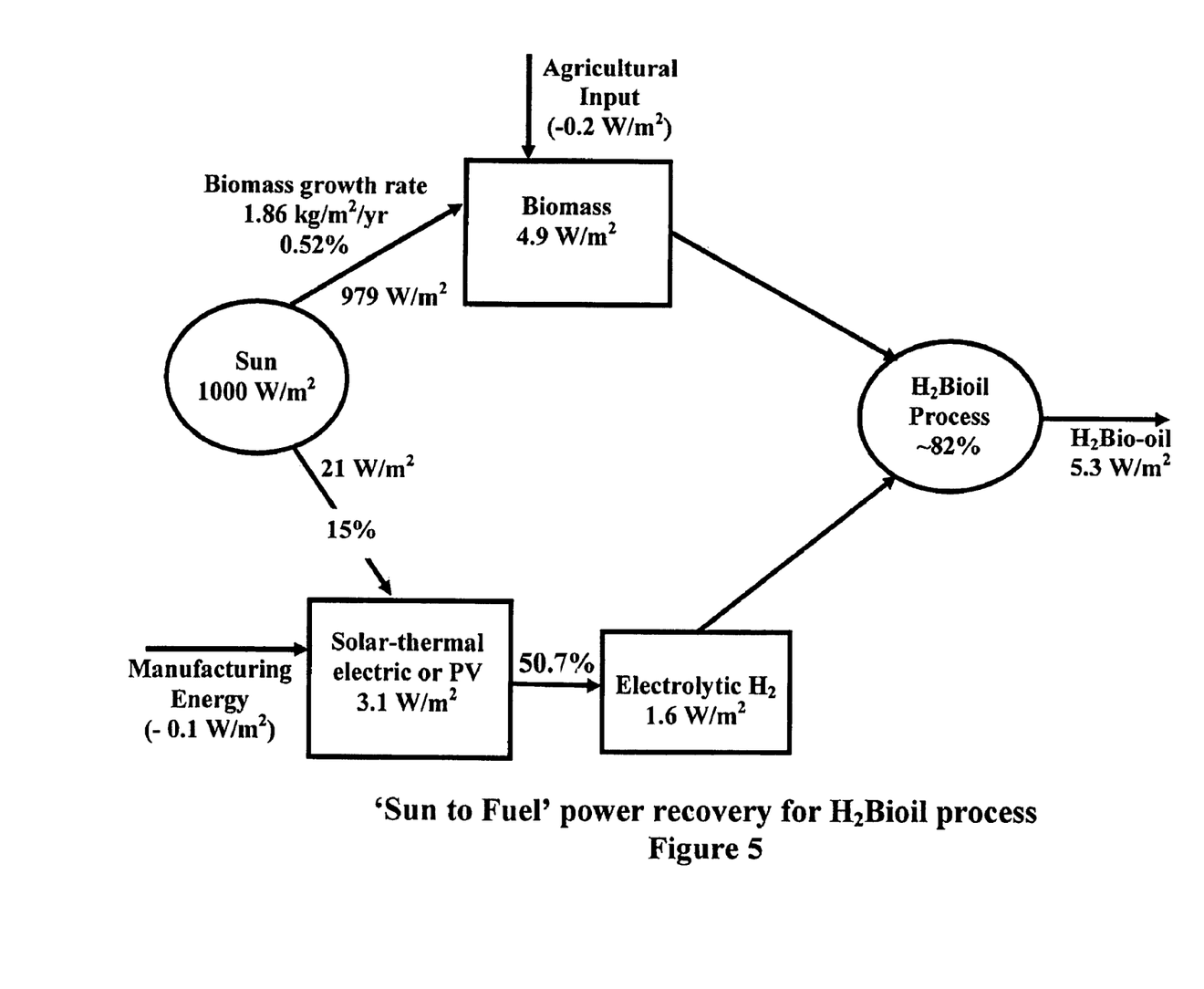
FIG. 5 depicts the 'Sun to Fuel' power recovery $H_2$Bioil process.

In an embodiment in accordance with the present invention, the total incident solar power is split to grow biomass (approximately 979 W) and produce $H_2$ by an electrolytic route (approximately 21 W). After accounting for approximately 15% efficiency of solar-thermal electric or PV and approximately 50.7% conversion efficiency of electricity to $H_2$, approximately 1.6 $W/m^2$ is available as $H_2$ for utilization in the $H_2$Bioil process. Similar efficiency for the hydropyrolysis are used in the $H_2$Bioil process (approximately 82%) of FIG. 4 where the power utilization for the $H_2$Bioil process is approximately 5.3 $W/m^2$, which is much higher than the other processes. The approach of directly utilizing $H_2$ from a carbon-free energy source increases the 'Sun to Fuel' power recovery as shown in FIG. 5. This illustrates a beneficial effect of injecting $H_2$ from a carbon-free energy source during the $H_2$Bioil process. It is worth noting that compared to the conventional pyrolysis process, the $H_2$Bioil process not only provides bio-oil with much higher energy density (approximately 42 MJ/kg vs. approximately 17 MJ/kg) but also recovers nearly 36% more energy from sun as liquid fuel. As compared to the conventional hydropyrolysis process of FIG. 4, the $H_2$Bioil process produces nearly 61% more bio-oil from a given quantity of solar energy. 'Sun to Fuel' power utilization can be further increased if process heat for $H_2$Bioil process is supplied from carbon-free source and char and gases are hydrogasified and converted to SNG.

While an exemplary embodiment incorporating the principles of the present invention has been disclosed herein, the present invention is not limited to the disclosed embodiment. Instead, this application is intended to cover any variations, uses, or adaptations of the inventions using its general principles. Further, this application is intended to cover such departures from the present disclosure as come within known or customary practice in the art to which this invention pertains and which fall within the limitations of the appended claims.

REFERENCE

The following are incorporated herein by reference in their entirety:
1. *The NRC report. The Hydrogen Economy—Opportunities, Costs, Barriers, and R&D Needs* 2004, Washington, D C: The National Academies Press.
2. Tarascon, J. M. and M. Armand, *Issues and challenges facing rechargeable lithium batteries*. Nature, 2001. 414 (6861): p. 359-367.
3. Hill, J., et al., *From the Cover: Environmental, economic, and energetic costs and benefits of biodiesel and ethanol biofuels*. PNAS, 2006. 103(30): p. 11206-11210.
4. Agrawal, R., et al., *Sustainable fuel for the transportation sector*. PNAS, 2007. 104(12): p. 4828-4833.
5. Rakesh Agrawal and Navneet R Singh, *Process for producing synthetic liquid hydrocarbon*. Pending U.S. Patent application Provisional No. 60/843,678, 2006.

6. Bridgwater, A. V., *Renewable fuels and chemicals by thermal processing of biomass.* Chemical Engineering Journal, 2003. 91(2-3): p. 87-102.
7. Huber, G. W., S. Iborra, and A. Corma, *Synthesis of Transportation Fuels from Biomass: Chemistry, Catalysts, and Engineering.* Chem. Rev., 2006. 106(9): p. 4044-4098.
8. Gercel, H. F., A. E. Putun, and E. Putun, *Hydropyrolysis of Extracted Euphorbia rigida in a Well-Swept Fixed-Bed Tubular Reactor.* Energy Sources, 2002. 24: p. 423-430.
9. Putun, A. E., et al., *Oil production from an arid-land plant: fixed-bed pyrolysis and hydropyrolysis of Euphorbia rigida.* Fuel, 1996. 75(11): p. 1307-1312.
10. Putun, A. E., et al., *Fixed-bed pyrolysis and hydropyrolysis of sunflower bagasse: Product yields and compositions.* Fuel Processing Technology, 1996. 46(1): p. 49-62.
11. Dilcio Rocha, J., C. A. Luengo, and C. E. Snape, *The scope for generating bio-oils with relatively low oxygen contents via hydropyrolysis.* Organic Geochemistry, 1999. 30(12): p. 1527-1534.
12. *The NRC report. The Hydrogen Economy—Opportunities, Costs, Barriers, and R&D Needs.* 2004.
13. Rosentrater, K. A., *Expanding the role of systems modeling: considering byproduct generation from biofuel production.* Ecology and Society, 2005. 11(1).
14. Graham, R. L., et al., *Current and Potential U.S. Corn Stover Supplies.* Agron J, 2007. 99(1): p. 1-11.

The invention claimed is:

1. A method for producing liquid hydrocarbons from biomass that contains carbon, the method comprising:
    forming hydrogen ($H_2$) from a carbon-free energy source; and
    hydropyrolizing the biomass to form bio-oil that comprises alkanes, alkenes, alcohols, aldehydes, ketones, aromatics, hydrocarbons or mixtures thereof, wherein hydropyrolizing comprises fast pyrolysis in a presence of $H_2$.

2. The method according to claim 1, wherein the carbon-free energy source includes at least one of solar energy, wind, hydropower and nuclear energy.

3. The method according to claim 1, wherein the biomass includes plant material, tree material, aquatic material or a mixture thereof.

4. The method according to claim 1, wherein the step of hydropyrolizing occurs in a hydropyrolysis reactor, the biomass reacting with the $H_2$ in the hydropyrolysis reactor to define fast hydropyrolysis.

5. The method according to claim 4, wherein residence time for fast hydropyrolysis is less than about one minute.

6. The method according to claim 4, wherein temperature during fast hydropyrolysis is between about 400 and 600° C.

7. The method according to claim 4, wherein the hydropyrolysis reactor contains a hydrodeoxygenation (HDO) catalyst for facilitating fast hydrolysis.

8. The method according to claim 4, wherein fast hydropyrolysis produces a gaseous exhaust stream and the method further comprises sending the gaseous exhaust stream from the hydropyrolysis reactor to a hydrodeoxygenation reactor.

9. The method according to claim 8, wherein the step of sending the gaseous exhaust stream includes removing char from the gaseous exhaust stream prior to being received by the hydrodeoxygenation reactor.

10. The method according to claim 8, wherein the hydrodeoxygenation reactor contains a hydrodeoxygenation (HOO) catalyst.

11. The method according to claim 8, wherein temperature of the gaseous exhaust stream being fed to the hydrodeoxygenation reactor is adjusted prior to being received by the hydrogenation reactor.

12. The method according to claim 11, wherein temperature of the hydrodeoxygenation reactor is lower than the temperature of the gaseous exhaust stream prior to being adjusted.

13. The method according to claim 8, wherein the hydrodeoxygenation reactor is a fixed bed reactor.

14. The method according to claim 8, wherein the hydrodeoxygenation reactor is a fluidized bed reactor.

15. The method according to claim 8, wherein effluent from the hydrodeoxygenation reactor is cooled to a condensed liquid bio-oil that is collected as a product stream.

16. The method according to claim 15, wherein the condensed liquid bio-oil is sent to a bio-oil upgrading reactor for upgrading prior to being collected as the product stream.

17. The method according to claim 16, wherein at least a portion of the $H_2$ from the carbon-free energy source is fed to the bio-oil upgrading reactor.

18. The method according to claim 8, wherein at least a portion of the $H_2$ from the carbon-free energy source is fed to the hydrodeoxygenation reactor along with the gaseous exhaust stream from the hydropyrolysis reactor.

19. The method according to claim 1, wherein process heat for pyrolizing the biomass is supplied from the carbon-free source in a form of at least one of electricity, heat and the $H_2$.

20. The method according to claim 1 further comprising:
    dividing the biomass into a first portion and a second portion, the first portion being directly converted by micro organisms to the liquid hydrocarbon;
    feeding the first portion to a direct conversion unit containing the microorganisms; and
    recovering the liquid hydrocarbons, a $CO_2$ containing stream and an unreacted biomass stream containing dried distillers grain solubles (DDGS),
    wherein the second portion of the biomass is pyrolized to the form bio-oil comprising alkanes, alkenes, alcohols, aldehydes, ketones, aromatics, hydrocarbons or mixtures thereof.

21. A method for producing liquid hydrocarbons from biomass that contains carbon, the method comprising:
    pyrolizing the biomass free from $H_2$ to form a reactor effluent stream;
    separating char from the reactor effluent stream;
    reacting the reactor effluent stream and $H_2$ to form upgraded bio-oil; and
    recovering the upgraded bio-oil.

22. The method according to claim 21, wherein temperature of the reactor effluent stream is adjusted prior to being fed to the hydrodeoxygenation reactor.

23. The method according to claim 22, wherein the unreacted biomass stream containing the DDGS is pyrolyzed.

24. The method according to claim 22, wherein processing energy for the direct conversion unit is supplied from the carbon-free source in a form of at least one of electricity, heat and the $H_2$.

25. A system for producing liquid hydrocarbons from biomass that contains carbon, the system comprising:
    a first unit configured to form hydrogen ($H_2$) from a carbon-free energy source; and
    a second unit configured to hydropyrolize the biomass in presence of $H_2$ to form bio-oil that comprises alkanes, alkenes, alcohols, aldehydes, ketones, aromatics, hydrocarbons or mixtures thereof, the $H_2$ being formed from using a carbon-free energy source.

* * * * *